United States Patent [19]

Törnblom

[11] Patent Number: 4,851,774

[45] Date of Patent: Jul. 25, 1989

[54] SUPPRESSION OF THE EFFECT OF HARMLESS SURFACE DEFECTS IN EDDY CURRENT TESTING BY SENSITIVITY CHARACTERISTIC COMPENSATION

[75] Inventor: Bengt H. Törnblom, Västeras, Sweden

[73] Assignee: Tornbloms Kvalitetskontroll AB, Vasteras, Sweden

[21] Appl. No.: 72,673

[22] Filed: Jul. 13, 1987

[30] Foreign Application Priority Data

Jul. 15, 1986 [SE] Sweden ............................... 8603113

[51] Int. Cl.[4] .................... G01N 27/72; G01N 27/82; G01R 33/12

[52] U.S. Cl. .................................. 324/225; 324/232; 324/242

[58] Field of Search .................... 324/225, 232, 242

[56] References Cited

U.S. PATENT DOCUMENTS 4,274,054 6/1981 Savidge et al. ..................... 324/225

4,355,281 10/1982 Toth et al. ........................... 324/242

FOREIGN PATENT DOCUMENTS 2041535 9/1980 United Kingdom .............. 324/225

Primary Examiner—Reinhard J. Eisenzopf
Assistant Examiner—Walter E. Snow
Attorney, Agent, or Firm—Watson, Cole Grindle & Watson

[57] ABSTRACT

An eddy current testing device for inspecting test objects, for example billets, with respect to surface defects, for example surface cracks, comprises at least one transducer/sensor, for example a surface transducer or surface transducer arrangement, which is made to scan the surface of the test object. The device is characterized in that the effect of harmless surface blemishes on the testing device is suppressed, at least partially, by compensating for the sensitivity characteristic, in the scan direction of the transducer/sensor, with respect to the surface defect.

2 Claims, 2 Drawing Sheets

SUPPRESSION OF THE EFFECT OF HARMLESS SURFACE DEFECTS IN EDDY CURRENT TESTING BY SENSITIVITY CHARACTERISTIC COMPENSATION

TECHNICAL FIELD

In eddy current testing the trend is towards an increasingly more widespread use of several carrier frequencies in order to overcome different types of problems, for example the suppression of the lift-off dependence and the like. One considerable, and limiting, factor in crack detection —now as well as previously —is, however, that harmless surface defects, i.e. surface defects in a test object which are not detrimental to any subsequent process step to which the test object will be subjected, give rise to false fault signals since they cannot be distinguished from the surface defects (e.g. cracks) which will be detrimental.

DISCUSSION OF PRIOR ART

In crack detection on hot continuously cast billets, so-called oscillation marks, for example, cause considerable problems in conventional testing. Swedish patent applications No. 7507857-6, 8302738-3, 8400698-0 corresponding to U.S. Pat. No. 4,661,177—filed on Feb. 8th 1985 in the name of Törnblom), and 8400861-4 (corresponding to U.S. Pat. No. 4,703,265 - filed on Feb. 15th 1985 in the name of T örnblom) describe methods and devices which may be regarded as part solutions to this problem. With the present invention in combination with the part solutions mentioned, a possibility is provided of efficiently suppressing the influence of oscillation marks on the crack detection process. The invention operates efficiently also as a separate invention, and together with, for example the disclosure set out in the afore-mentioned U.S. patent applications, it provides an almost complete solution.

The reason for the previously experienced difficulties in pluri-frequency eddy current testing is primarily to be found in the unwanted effects caused by the different depth of current penetration of the different carrier frequencies used adjacent to an oscillation mark and the like harmless surface defect, because of the variation in inductive coupling arising in that connection, as a function of the position of the transducer, between the transducer and the test object.

The existing specialist literature as —far as is known —does not describe any method, nor mention any means, which determines the causes of the problems discussed, or how they can be overcome and solved.

It should be pointed out in this connection that one reason why the problem has now become open to analysis and explanation is the introduction of the imaginary sum currents which are described in the above-mentioned U.S. patent application and which are also employed as the basis of the explanation of the present invention given herein.

Since all conventional eddy current transducers provided with a center hole in the winding normally suffer from the deficiencies mentioned here, the present invention should therefore result in a marked improvement of the theoretical limit to the minimum size of cracks that are detectable in relation to the level of occurrence of oscillation marks and the like, compared with current technique.

The above-mentioned U.S. patent applications, incorporated herein by reference, describe methods and means by which a vector transformation or the like can be optimised over the lift-off (LO) operating range by carrying out the transformation as a function of the LO distance, and also describe how to compensate for the various depths of the sum currents by a special design of the transducer. Common to the inventions disclosed in these earlier U.S. patent applications is that &hey are primarily effective in suppressing undesired effects caused by a varying lift-off in combination with the varying depths of penetration of the currents induced by the different carrier frequencies. In other words, variations in height of the transducer (measured perpendicular to the surface of the test object) can be suppressed. However, the inductive coupling between the transducer and the surface of the test object is dependent not only on the distance (LO) but also on &he length of the surface current path covered by the transducer coil in the transverse direction (along the surface). Therefore, the present invention, which also permits harmless surface defects with a longitudinal/transverse extension to be ignored, is to be considered an important complement to the above-mentioned U.S. patent applications, by means of which a more three-dimensional possibility of suppression is obtained. Taken together, these inventions then permit, for example, an efficient suppression of the unwanted influence on, for example, a crack detection operation, of the presence of oscillation marks and the like harmless surface defects.

SUMMARY OF THE INVENTION

According to the invention a device utilizing eddy current techniques for inspecting a test object for surface defects, for example surface cracks, comprising at least one transducer/sensor, which is made to scan the surface of the test object, is characterized in that the effect of harmless surface blemishes on the transducer/sensor is suppressed, completely or partially, by the device being compensated for the sensitivity characteristic, in the scan direction with respect to the surface blemish.

The invention will now be described, in somewhat simplified terms as follows. It should be pointed out, however, that both the description and the accompanying drawings are to be considered one of many feasible alternatives or examples of how the invention can be realized. The drawings are not accurate as far as scales and dimensions are concerned and are to be regarded as examples illustrating the principle of the invention.

To make the description more easily comprehensible, mathematical derivations have been replaced by relevant —in some cases approximate —reasonings which, despite their simplicity, are well founded both in theory and in practice. For the same reason, both the description and the drawings have been based on the use of only two carrier frequencies. However, the invention does, of course, include the use of more than two frequencies or complexes of frequencies.

BRIEF DESCRIPTION OF THE DRAWINGS

The invention will now be further described by reference to the accompanying drawings, in which.

FULLER DESCRIPTION OF THE INVENTION AND PREFERRED EMBODIMENTS

Figure 1:
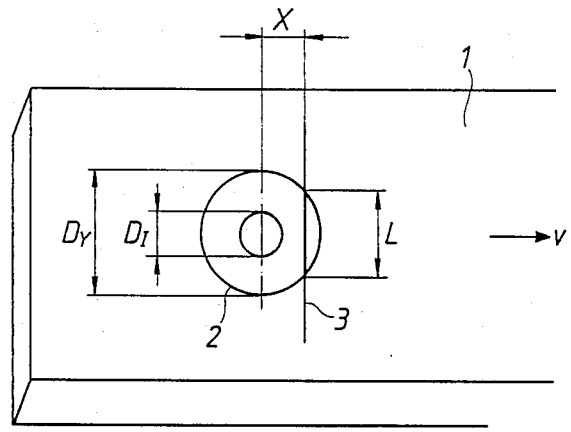
FIG. 1 is a schematic view, from above, of a sensing transducer used for defect detection supported over a moving test object.

FIG. 1 shows a test object in the form of a billet exhibiting on its upper surface an oscillation mark 3 (hereinafter abbreviated as "oscm"). A conventional circular surface transducer 2 of external diameter $D_Y$ and internal diameter $D_I$ moves over the surface of the billet 1 at a constant height above the surface and at a constant speed of v m/s.

The way FIG. 1 has been drawn, the transducer winding overlies only a length L of the total length of the oscm. This length L will, of course, vary as the transducer winding moves across the oscm, that is to say, L is a function of X in FIG. 1. For reasons which will be easily understood, the inductive coupling between the transducer winding and the surface of the billet is greatest directly below the winding.

Since in practice, the oscm almost invariably has an extension extending transversely across the billet 1, and its width W (see FIG. 2) is small in relation to the external diameter $D_Y$ of the winding 2, the change/disturbance of the magnetic field caused by the oscm will approximately be proportional to the length L. This then means that the impedance of the winding 2 varies in a manner similar to that in which L varies as the winding 2 passes over the oscm. Since the winding 2 has a hole or core in the center, which is the case with all crack-detection transducer windings known to me, a plot of L as a function of X will be similar to graph 5 in FIG. 3, which is an important statement for an appreciation of this invention. The dip shown centrally in the peak of graph 5 in FIG. 3 is therefore—to anticipate the reasoning somewhat —a consequence of the internal hole (with the diameter $D_I$) in the winding 2.

The extended shape of the oscm, and the simplicity of showing L as a function of X, facilitates the understanding of the principle behind the invention. In general terms, however, for all uncompensated coils the rule applies that they always have sensitivity characteristic functions at differing carrier frequencies which exhibit the difference D.

Figure 2:
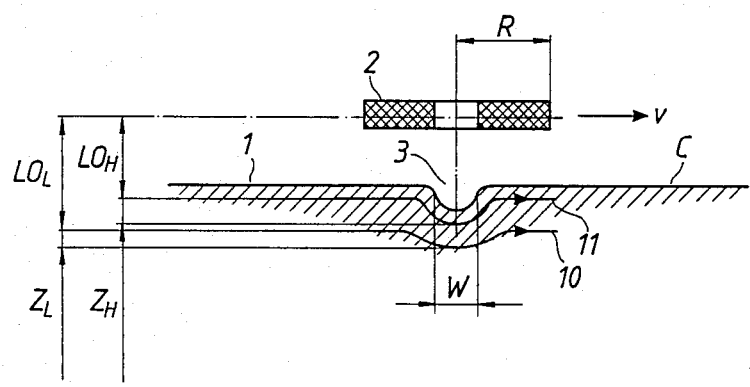
FIG. 2 is a partial sectional view, on an enlarged scale, showing a sensing transducer and the high and low frequency currents induced in the surface region of a test object by the transducer.

FIG. 2 is an enlarged sectional view of a transducer winding 2 supported over the surface of a test object 1 which contains a surface blemish 3. The winding is fed with currents at two different frequencies which give rise to induced currents 10 and 11 at different distances below the surface of the object 1. The sum currents 10 and 11 shown are the same imaginary currents as are shown in FIGS. 1 and 2 of U.S. Pat. No. 4,703,265 and in FIG. 1 in U.S. Pat. No. 4,661,777.

Figure 3:
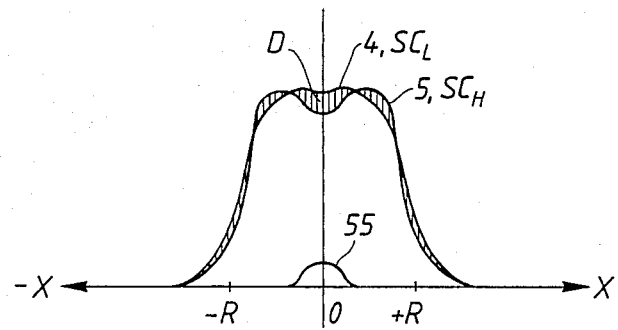
FIG. 3 is a graph showing the electrical output of the sensing transducer as a function of X as a harmless surface defect moves past the transducer.

FIG. 3 shows, as explained above, the sensitivity characteristic (hereinafter abbreviated to "SC") of the transducer/sensor 2 for a certain type of surface blemish, in this case an oscm. Thus, SC is the sensitivity curve sensed by the transducer/sensor 2 in passing over an oscm. The graph is plotted as a function of X, at a certain LO-distance. X=0 has been selected to represent the position where the transducer winding is situated exactly above the oscm.

Because currents of different frequencies are influenced somewhat differently by an oscm, two SC's are shown in FIG. 3, i.e. one for each respective carrier frequency. Curve 4 shows $SC_L$ (low frequency) and curve 5 shows $SC_H$ (high frequency). When the oscm 3 passes under the transducer winding 2, the sum currents of the high 11 and low 10 frequencies, respectively, will be depressed by $Z_H$ and $Z_L$, respectively, by the oscm, as is shown simplified in FIG. 2.

As is also clear from FIG. 2, $Z_H/LO_H > Z_L/LO_L$, which means that the impedance change caused by the oscm in the transducer winding 2 is relatively greater for the high frequency current than for the low frequency current. This is one of the reasons for the dip on the $SC_L$-curve being less significant than the dip on the $SC_H$-curve. The result of this is that the oscm will give rise to different SC-curves for the different carrier frequencies which are used. The consequence of this, in turn, is that a difference D is obtained between the curves 4 and 5 which is shown shaded in FIG. 3. Depending on the shape of the winding 2 etc., this difference D may contain primarily second and third harmonics but in certain cases also harmonics of a higher order.

Both the difference D per se and its harmonic content are greatly disturbing for all types of signal processing, for example a transformation, in which at least two carrier frequencies are used, since crack detection is normally based on some type of difference measurement between the frequencies. An example of such a difference measurement is given in the above-mentioned Swedish patent application No. 7507857-6. The difference D can here be directly or indirectly construed as a crack (i.e. a nonharmless blemish), which of course is a considerable disadvantage.

By imparting to different parts of the transducer/sensor different sensitivites in the direction of relative movement of the transducer past the object 1 as a function of the carrier frequency in question, it is possible to compensate for the difference D. Such a compensation will be referred to as a sensitivity characteristic compensation (hereinafter abbreviated to "SCC"). It should be mentioned that the SC-functions, including the SCC-function, may involve more than just the transducer and its windings. Thus, the SC-function may also, for example, comprise —completely or partially—the rest of the crack testing or measuring device.

The invention proposes both a method and a device for limiting, completely or partially, the effects on the crack detection process caused by the difference D and/or its harmonics or frequency contents. Both the SC-functions for harmless surface deformations and the difference between different SC-functions of different frequency origins, when using at least two carrier frequencies, are novel both as regards the definition and as regards the possibilities of understanding and remedying the undesired effects caused by different depths of current penetration. This is the reason why the invention can be considered to be characterized by the device as described in the Summary of the Invention given above.

According to the invention harmless surface deformations, such as oscillation marks and the like, can be suppressed, completely or partially, by the sensitivity characteristic (SC) for the surface deformation in question being largely the same or similar for/at at least two different carrier frequencies and/or complexes of carrier frequencies. The SC's, which are largely similar for the carrier frequencies or complexes of carrier frequencies in question, may be obtained, completely or partially, by signal processing, for example amplifying, signals from at least one part of the transducer/sensor or the transducer/sensor arrangement, as a function of the carrier frequency in question. Thus, an SC-function can be formed, for example, by attenuating or amplifying signals of a certain frequency from a limited part of the transducer winding, which signals are then, for example, added to the other signals from the transducer winding of the same frequency origin. It is possible to obtain, completely or partially, the SC-functions, which are largely the same or similar for the carrier frequencies occurring at a particular time, by supplying parts of or a part of the transducer winding, having different surface coverage, completely or partially with different carrier frequencies or carrier frequency components.

Another characteristic feature may be that at least one transducer/sensor includes at least two windings (or loops) of different dimensions and/or shapes. By making, for example, a part of the transducer/winding adjustable relative to the rest of the arrangement, the optimum SC-function for the surface deformation in question can be tested in a simple manner. As an example, a small coil can be screwed out of or into a larger coil in order thus to optimize the SC-function. Another way of achieving a suitable SC-function is to form the coil so that it, per se, exhibits a suitable characteristic, which normally presupposes a non-square or rectangular shape of the cross section of the winding. By making the ratio $D_Y/D_I$ large, for example $>5$, the dip on the SC-curve is reduced, which may in certain cases be a sufficient compensation.

If it is desired to obtain maximum performance, it may be suitable to minimize the difference D in FIG. 3 further, in addition to what can be carried out at the transducer winding. This can be done, for example, by signal processing, for example shaping, signals originating from completely or partially different carrier frequencies, for example rectified carrier frequency signals, differently prior to the transformation and the like, since in that case the transformation is not disturbed.

Figure 4:
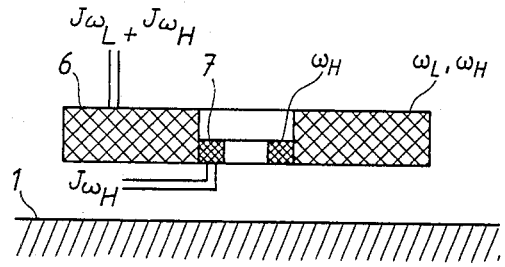
FIGS. 4 and 5 show, in transverse cross-section two embodiments of sensing transducer for use in a device according to the invention.
Figure 5:
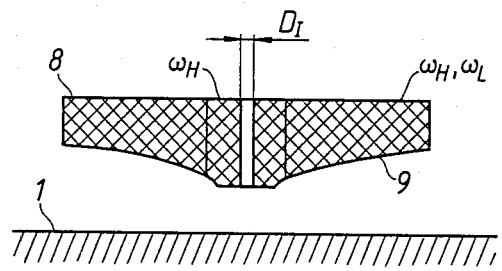

In eddy current testing, magnetic fields of a relatively high frequency are used, which may, for example, be generated by supplying a winding from a so-called constant current generator with current of different carrier frequency contents. In this way, one winding may act both as a primary coil and as a secondary coil or —where desired —as the transducer and as the sensor at the same time. FIGS. 4 and 5 may therefore, for the sake of simplicity, be regarded as a transducer/sensor with a common primary and secondary winding. Thus, the current supply and the sensing can take place via the same connection, if this is desired. However, the current generators have been omitted in these Figures so as not to confuse matters.

Figure 6:
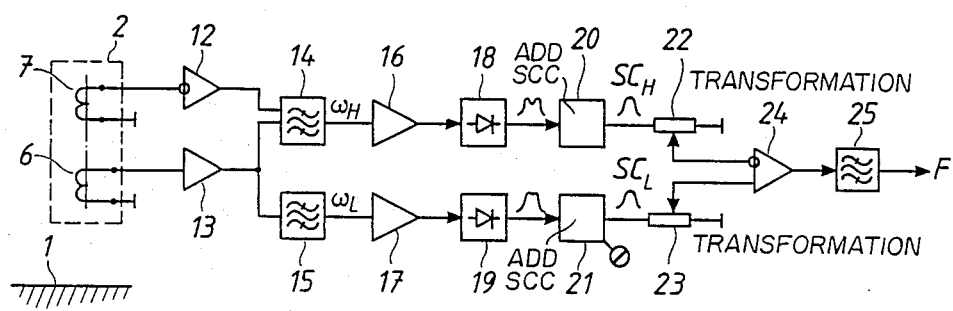
FIG. 6 shows a simplified block diagram of crack detection equipment in accordance with this invention.

FIG. 4 shows a transducer/sensor comprising two coils 6 and 7 of different sizes and shapes. These coils are also shown in FIG. 6. The larger coil 6 is sensed with respect to both the carrier frequencies, i.e. $\omega_L$ and $\omega_H$, whereas the smaller coil 7 is only sensed with respect to the high frequency $\omega_H$, which is also clear from FIG. 6. The SC-function from the larger coil 6 may then, for example, have the appearance as illustrated in FIG. 3. However, by subtracting from curve 5 in FIG. 3 the contribution obtained from the smaller coil 7, placed at the center of the transducer, the dip in curve 5 can be reduced and hence be made equivalent to that in curve 4. In this way the difference D is completely suppressed and resultant optimum SC-functions are obtained which are insensitive to harmless surface blemishes.

Because of the fact that the smaller coil 7 has smaller dimensions, for example —as in this case—a smaller diameter, its SC-function (curve 55 in FIG. 3) will have a more limited extension than that of the larger coil 6. It is then readily appreciated that its dimension can be adapted so as to become optimal with respect to the difference that it is to be compensated for.

FIG. 5 shows an alternative form of transducer/winding, in which one coil 8 is fed, for example, from a constant current generator, containing the carrier frequencies $\omega_H$ and $\omega_L$, at one point and with only $\omega_H$ at another point. In this way, with an equivalent reasoning, sensibly the same result can be obtained as with the transducer/winding shown in FIG. 4.

In principle, it is possible to design transducers/sensors comprising an unlimited number of windings of, for example, different shapes and dimensions, and to allow these to cooperate so that SC-functions are created which are suited for suppression of an arbitrary type of surface blemish. It will then be possible to combine parallel or series-connected channels in signal processing equipment in which, for example, the task of each respective channel is to suppress the effect of a specified type of surface blemish.

In the same way as the effect of surface blemishes can be suppressed, SC-functions can be created which emphasize harmful blemishes in the surface, for example cracks. "Tailoring" a transducer for detection of a certain type of surface blemish or other defect is then the inverse use of the invention.

FIG. 6 shows a simplified block diagram of one form of crack detection equipment. The transducer/sensor comprises two windings 6, 7. The output signals from these are amplified in amplifiers 12 and 13 and are then filtered in a band pass filter 14 with respect to the high frequency and in a band pass filter 15 with respect to the low frequency. Since the signals from coil 7 and amplifier 12 are only supplied to the filter 14, the coil 7 only provides a contribution to the high frequency signal, which means the SCC of that part of, for example, the billet surface which is covered by the coil 7, or better still, that part of the transducer/sensor 2 which is represented by the coil 7. The output signals from the filters 14 and 15 are further amplified in respective amplifiers 16 and 17 and are then rectified in respective phase-sensitive rectifiers 18 and 19. In case the above-mentioned SCC is not sufficiently efficient, it may be justified to perform an additional SCC of the rectified signals, which in FIG. 6 is effected electronically in the blocks 20 and 21, which may comprise summation amplifiers. These can perform in certain cases, signal processing which may include, for example, filtering, adjustable signal delay, pulse shaping and so on, and results in the finally SCC-compensated SC-functions $SC_H$ and $SC_L$, respectively, which constitute input signals to subsequent transformation blocks 22, 23 and 24. As will have been clear from the above, the original SC-functions have been compensated for both by the transducer/sensor arrangement used and by the signal processing undertaken. The amplitude of the SC-functions is suitably adapted to, for example, the current transformation setting. If, for example, the transformation is chosen for optimum LO-suppression, a suitable SC-amplitude is chosen among the functions, starting from the current transformation setting. A band pass filter 25 finally filters out a current fault signal F, representing, for example, the presence of a crack on the billet surface or other harmful blemish on the test object.

Since the SCC is carried out prior to vector transformation, the existence of harmless surface deformations does not, of course, influence the possibility for reliable crack detection.

Scope of terms used in the Specification

By SENSITIVITY CHARACTERISTIC (SC) is meant the —e.g. normative—sensitivity function/curve which is obtained upon relative movement of the transducer/sensor past a harmless surface blemish or harmful defect. The SC refers to a certain carrier frequency or complex of carrier frequencies, and to a certain surface blemish, and in some cases also to a suitable LO-distance.

By SENSITIVITY CHARACTERISTIC COMPENSATION (SCC) is meant that the difference (D) and/or the differences between different original SC-functions is/are completely or partially compensated for or balanced out.

By CARRIER FREQUENCY is meant the frequency of that current which generates a magnetic field, in other words, the frequency of the transducer current.

By TRANSFORMATION and VECTOR TRANSFORMATION is meant for example, vector transformation as described, for example, by Libby in U.S. Pat. No. 4,303,885, in Swedish Patent No. 7507857-6, and, inter alia, in U.S. Pat. No. 4,661,777.

By TEST OBJECT is meant, for example, a hot billet, a sheet, a tube or a section.

By LO-DISTANCE is meant the lift-off, i.e. the distance between the transducer/sensor and the surface of the test object.

By TRANSDUCER is means any type of transducer and/or sensor operating with or being otherwise sensitive to a magnetic field. The term transducer can, for example, include everything from a simple loop to complicated coil arrangements of a three-dimensional nature.

A surface deformation, for example an oscm, normally differs from a crack (see C in FIG. 2) by having a greater width (W) in the scan direction v than the crack.

In the case of rotary symmetrical transducer embodiments it is simple, for obvious reasons, to perform an SCC on the transducer in all directions of movement, which means that the transducer may have an arbitrary direction of movement with a retained SCC.

The invention can be varied in many ways within the scope of the following claims.

I claim:

1. An eddy current sensing device for monitoring a test object for the presence of surface defects, comprising:
   at least one sensing transducer adapted to move relative to at least a part of the surface of the test object for scanning said surface and including at least two windings of different shape;
   means for supplying at least partially separate parts of said sensing transducer with currents of different carrier frequencies; and
   means for reducing the sensitivity characteristic of the sensing transducer in the direction of scanning movement with respect to each harmless surface deformation at least partially by processing differently said current carrier frequencies from at least two at least partially separate parts of said sensing transducer.

2. An eddy current sensing device for monitoring a test object for the presence of surface defects, comprising:
   at least one sensing transducer adapted to move relative to at least a part of the surface of the test object for scanning said surface and including at least two windings of the same shape but of different dimensions;
   means for supplying at least partially separate parts of said sensing transducer with currents of different carrier frequencies; and
   means for reducing the sensitivity characteristic of the sensing transducer in the direction of scanning movement with respect to each harmless surface deformation at least partially by processing differently said current carrier frequencies from at least two at least partially separate parts of said sensing transducer.

* * * * *